United States Patent
Takashima

(10) Patent No.: US 6,802,850 B1
(45) Date of Patent: Oct. 12, 2004

(54) PROSTATE MASSAGE APPARATUS

(76) Inventor: Jiro Takashima, 7203 Schiller, Houston, TX (US) 77055

( * ) Notice: Subject to any disclaimer, the term of this patent is extended or adjusted under 35 U.S.C. 154(b) by 323 days.

(21) Appl. No.: 09/675,436

(22) Filed: Sep. 29, 2000

(51) Int. Cl.⁷ .......................... A61H 7/00; A61M 29/00
(52) U.S. Cl. ........................ 606/197; 601/177; 601/136
(58) Field of Search .............................. 606/197, 191; 601/134, 135, 136, 137

(56) References Cited

U.S. PATENT DOCUMENTS

| | | | |
|---|---|---|---|
| 547,076 A | * 10/1895 | Hubbell | 606/197 |
| 812,679 A | * 2/1906 | Reimanns | 606/197 |
| 1,327,786 A | * 1/1920 | Stephan | 606/197 |
| 2,184,642 A | * 12/1939 | Glass | 607/113 |
| 2,478,786 A | 8/1949 | Smallen | |
| 3,675,642 A | * 7/1972 | Lord | 606/197 |
| 4,542,753 A | 9/1985 | Brenman | |
| 4,583,542 A | * 4/1986 | Boyd | 606/197 |
| 5,404,881 A | 4/1995 | Cathaud | |
| 5,797,950 A | 8/1998 | Takashima | |
| 5,861,000 A | 1/1999 | Takashima | |

* cited by examiner

Primary Examiner—Michael A. Brown
Assistant Examiner—Benjamin K. Kou
(74) Attorney, Agent, or Firm—Harrison & Egbert

(57) ABSTRACT

An apparatus for massaging a prostate gland by a contraction of a sphincter including a head and a resistor section. The head has a size suitable for fitting into a human rectum and through the sphincter. The head has a bulbous upper portion and a tapered section extending from the upper portion. The tapered section narrows in diameter from the upper portion. The resistor section is connected to a bottom of the head. The resistor section has a tapered surface widening from the bottom of the head. The tapered surface of the resistor section has an angle of taper smaller than an angle of taper of the tapered section at the bottom of the head. The resistor section is adapted to movably hold the tapered section of the head within the sphincter.

2 Claims, 1 Drawing Sheet

PROSTATE MASSAGE APPARATUS

TECHNICAL FIELD

The present invention relates to apparatus for the treatment of prostatitis. More particularly, the present invention relates to devices for massaging the prostate gland.

BACKGROUND ART

One treatment for non-bacterial disorder of prostate such as chronic prostatitis and a congested prostate is the prostate massage. Some urologists believe that the most effective treatment for such prostatitis is for the doctor to massage the prostate at regular intervals. Other urologists are far less enthusiastic about this procedure, and some do not believe in it at all. To perform such a massage, the physician simply inserts a gloved finger into the rectum and strokes the prostate very gently. It serves to relieve the symptoms of chronic prostatitis by draining accumulated prostatic fluid from the glands and ducts.

Given the difference of opinion of urologists as to the need for prostatic massages, such massages can be difficult to obtain. In any event, the regular and repeated massaging of the prostate can often require frequent visits to the doctor's office. This causes the patient to incur a considerable expense and inconvenience. As such, a need has developed for allowing an individual to carry out his own prostatic massage.

In the past, some patents have issued relating to rectal devices. U.S. Pat. No. 4,542,753, issued on Sep. 24, 1985 to Brenman et al. describes an apparatus and method for stimulating penile erectile tissue. In this invention, a body is provided which may be inserted into the rectum of a user. The body is shaped so as to closely conform to the topological configuration of the rectum within the anal area to a site adjacent to the prostate gland. Electrical circuitry for generating a neurally stimulating electrical signal is located within the body. Electrodes, placed at particular locations on the surface of the body, apply the signal to the user. At least one of the electrodes closely contacts the prostate gland when the body member is operatively disposed, at a region or spot on the prostate gland previously determined to be sensitive to electrical stimulation.

U.S. Pat. No. 5,404,881, issued on Apr. 11, 1995, to Cathaud et al. describes a trans-rectal probe. This trans-rectal probe includes a probe body made of a flexible self-supporting polymer material whose degree of flexibility is designed to enable it to comply with the shape of the rectum while having substantially no compression effect on the rectum when inserted therein. The invention makes it possible to achieve accurate, safe and reliable positioning or an instrument for detection or therapeutic treatment level with the organ to be observed or treated. In particular, this device is designed for treatment of the prostate.

U.S. Pat. No. 2,478,786, issued on Aug. 9, 1949 to H. M. Smallen, describes a prostate gland massaging implement. This implement includes a lever having an interior handle which constitutes a power arm to extend down in front of the abdomen and a substantially horizontal portion extending under the groin and offset laterally to avoid the genital organs. The implement has an upwardly and forwardly bent posterior portion which forms the work arm. This work arm extends into the rectal passage to bear across the frontal wall thereon adjacent the prostate gland. The bent portion between the horizontal and the posterior portions serves as a fulcrum point against the front wall of the rectal opening when the implement is subject to pivotal movement around this point The present inventor has two United States patents showing devices for releasing congested prostate fluid. U.S. Pat. No. 5,797,950, issued on Aug. 5, 1998, describes such a device including a head having a size suitable for fitting in a human rectum and through a sphincter. The head has a size suitable for rubbing the prostate gland. A rod is connected to the bottom of the head and extends outwardly therefrom. The rod serves to position the head and guide a movement of the head as the sphincter contracts and relaxes. An abutment surface is affixed to the rod distal the head. The abutment surface contacts the perineum area and pushes up on the perineum area as the sphincter contracts. The rod is a rigid rod having a generally L-shaped or C-shaped configuration with a radius of curvature such that the head tilts toward the prostate gland as the sphincter contracts and draws the head upwardly. The head has a generally ellipsoidal shape.

U.S. Pat. No. 5,861,009, issued on Jan. 19, 1999, to the present inventor, describes an apparatus for releasing congested prostate fluid having a head with a size suitable for fitting into a human rectum and through the sphincter and having a surface for pushing on the prostate gland. A rod is connected to the bottom of the head and extends outwardly therefrom so as to guide a movement of the head as the sphincter relaxes and contracts. An abutment member is positioned on the rod opposite the head so as to push on the perineum area simultaneously with the head pushing on the prostate gland. The abutment member has a variable angular relationship with the head.

In each of these prior art patents to the present inventor, when the external sphincter contracts, the lateral pressure of the external sphincter drives the head upwardly and the rod adds pressure against the perineum area simultaneously. The power of the sphincter's contraction is divided into one for pressure on the prostate and one for pressure onto the perineum area. Under certain circumstances, some persons have felt that the perineum pressure by this rod was strong and uncomfortable.

It is an object of the present invention to provide an apparatus which enables persons to carry out self-massages of the prostate so as to express the fluid from this congested prostate.

It is another object of the present invention to provide a prostate massage apparatus which reduces the amount of pressure applied to the perineum area.

It is a further object of the present invention to provide a prostate massage apparatus which facilitates the ability of the users to control the position of the head of the prostate massage apparatus within the rectum through the application of rectal pressure and sphincter contraction.

It is a further object of the present invention to provide such a prostate massage apparatus which is safe, easy to use and relatively inexpensive.

These and other objects and advantages of the present invention will become apparent from a reading of the attached specification and appended claims.

SUMMARY OF THE INVENTION

The present invention is an apparatus for massaging a prostate gland by a contraction of a sphincter comprising a head and a resistor section. The head has a size suitable for fitting into a human rectum and through the sphincter. The head has a bulbous upper portion and a tapered section extending from the upper portion. The tapered section narrows in diameter from the upper portion. The resistor section is connected to the bottom of the head. The resistor section has a tapered surface widening from the bottom of the head. The tapered surface of the resistor section has an angle of taper smaller than an angle of taper of the tapered section at the bottom of the head. The resistor section is adapted to movably hold the tapered section of the head within the sphincter.

In the present invention, the tapered section of the head and the resistor section have a total length greater than a length of the sphincter. Specifically, the tapered section of the head has a length greater than one-half the length of the sphincter. Also, the tapered surface of the resistor section has a length greater than one-half the length of the sphincter. The resistor section has a bottom with a narrower diameter than a diameter of the tapered section of the head. The tapered surface widens to a point from the bottom of the head. The tapered surface narrows from this point toward a bottom of the resistor section. The tapered surface section has an angle of taper toward the point which is greater than an angle of taper of the tapered section from the point to the bottom of the resistor section. The bottom of the resistor section has a diameter less than a diameter of the bottom of the head. A rod can be connected to a bottom of the resistor section.

DETAILED DESCRIPTION OF THE INVENTION

Figure 1:
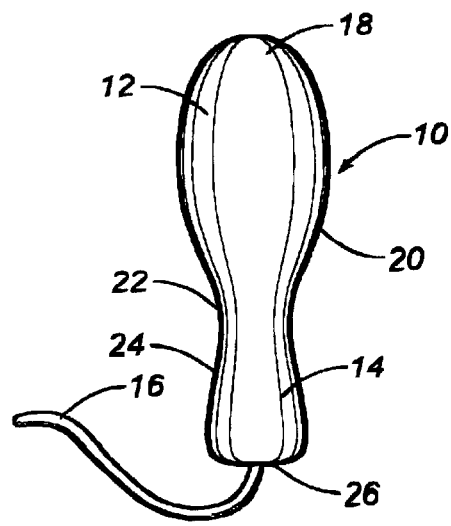
FIG. 1 is a side elevational view of the preferred embodiment of the present invention.

Referring to FIG. 1, there is shown at 10 the prostate massage apparatus in accordance with the preferred embodiment of the present invention. The prostate massage apparatus includes a head 12, a resistor section 14 and a rod 16. The head 12 has a size suitable for fitting into a human rectum and through the sphincter. The head 12 includes a bulbous upper portion 18 and a tapered section 20 extending from this upper portion 18. The tapered section 20 narrows in diameter from the upper portion toward a point 22 which is joined to the resistor section 14.

The resistor section 14 is connected to the bottom 22 of the head 12. The resistor section 14 has a tapered surface 24 widening from this point 22 at the bottom of the head 12. The tapered surface 24 of the resistor section 14 has an angle of taper which is smaller than the angle of taper than the tapered section 20 of the head 12. The resistor section 14 is adapted to hold the tapered section 20 of the head 12 within the sphincter.

The rod 16 is connected to the bottom 26 of the resistor section 14 and extends outwardly therefrom so as to contact the perineum area of the user and to add a back tension to the head 12 so that the rod 16 movably retains the tapered section 20 of the head 12 within the tile portion. of the sphincter. When the sphincter contracts, the lateral pressure applied to the tapered section 20 of the head 12 pushes the head 12 upwardly while the rod 16 simultaneously applies a pressure to the perineum area.

In FIG. 1, it can be seen that the head 12 has a bulbous upper portion 18 having a construction similar to that described in prior U.S. Pat. Nos. 5,797,950 and 5,861,000 to the present inventor. The head 12 has a sufficient diameter and taper so as to hold the head 12 within the rectum against the rectal pressure when the sphincter relaxes. The resistor 14 is attached to the bottom of the head 12. The resistor 14 can act similarly to the rod described in prior U.S. Pat. Nos. 5,797,950 and 5,861,000 so as to movably hold the tapered section 20 of the head 12 within the tile portion of the sphincter. The resistor 14 has its tapered surface 24 widen toward the bottom 26 of the resistor 14. The resistor 14 provides a counteraction against the upward movement of the head 12 caused by a lateral pressure of the internal and external sphincter so that the tapered section 20 of the head 12 is movably held within the tile portion of the sphincter. The angle of taper of the tapered surface 24 of the resistor 14 is smaller than the angle of taper of the tapered section 20 in the area a above the point 22 at the bottom of the head 12. Area "a" represents one-half the length of the tile portion of the sphincter. The total length of the tapered section 20 and the tapered surface 24 will be greater than the length of the sphincter. Similarly, the tapered section 20 will have a which is greater than one-half the length of the sphincter. The tapered surface will similarly have a length which is greater than one-half the length of the sphincter.

The rod 16 is connected to the bottom 26 of the resistor 14. The rod 16 will contact against the perineum area so as to movably hold the tapered section 20 of the head 12 within the tile portion of the sphincter along with the resistor 14.

Figure 2:
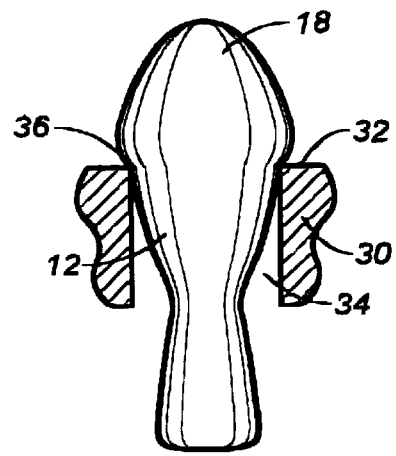
FIG. 2 is an isolated view showing the apparatus as initially inserted into the rectum.

FIG. 2 shows the first position of the apparatus 10 when the external sphincter 30 is in a relaxed state. The upper portion 18 of the head 12 was inserted through the sphincter 30 and into the rectum. The bulbous upper portion 18 of the head 12 has a sufficient diameter so as to hold the upper portion 18 of the head 12 by the upper edge 32 of the sphincter 30. The tapered section 20 of the head 12 is movably suspended within the tile portion 34 of the sphincter 30 against a rectal pressure. A step 36 is formed between the bulbous upper portion 18 of the head 12 and the tapered section 20 of the head 12. This step 36 serves to retain the upper portion 18 of the head 12 within the human rectum.

Figure 3:
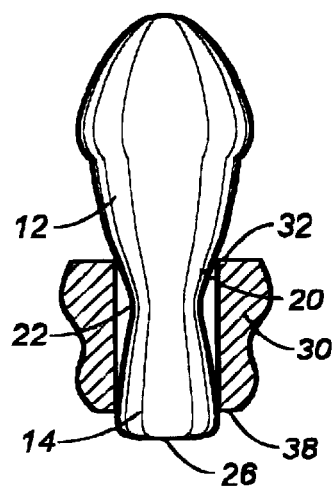
FIG. 3 is a diagrammatic illustration showing the action of the sphincter upon the surfaces of the apparatus.

FIG. 3 shows another position of the apparatus 10 of the present invention. In FIG. 3, it can be seen that the resistor 14 has its tapered surface 24 widening from the bottom point 22 of the head 12 toward the bottom 26 of the resistor 14. When the sphincter 30 contracts, the strong lateral thrust force of the sphincter 30 onto the tapered section 20 of the head 12 pushes the head 12 upwardly against the counteraction provided by the resistor 14 and the rectal pressure. This will continue until the upper edge 32 of the sphincter 30 attains the same diameter as the lower edge 38 of the sphincter 30. The size of the opening of the sphincter 30 at the upper edge 32 is controlled by the position of the tapered section 20 of head 12 at that area. Similarly, the size of the opening of the sphincter 30 at the bottom edge 38 is controlled by the shape of the tapered surface 24 of the resistor 14 in that area. As a result, the length of the movement of the head 12 by the lateral force of the sphincter 30 is limited to a distance less than the length of the sphincter. The narrowing of the angle of taper of the tapered surface 24 of the resistor 14 to an angle narrower than the angle of taper of the tapered section 20 of the head 12 creates a longer movement of the resistor 14. As a result, movement nearly through the entire length of the tile portion 34 of the sphincter 30 can be achieved.

When the angle of taper of the resistor 14 is wider than the angle of taper of the tapered section 20 of the head 12, then the length of movement of the resistor 14 will be limited to less than one-half the length of the tile portion of the sphincter.

Figure 4:
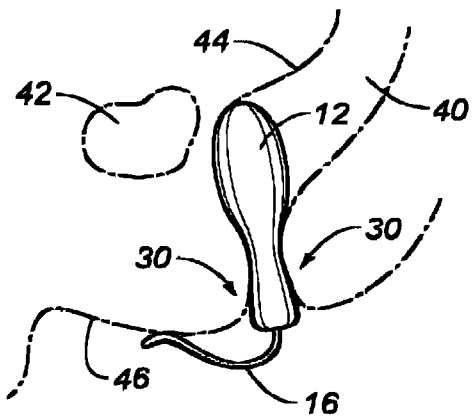
FIG. 4 is a cross-sectional view showing the actual application of the device within a human rectum.

FIG. 4 illustrates the apparatus 10 as located within the rectum 40. In FIG. 4, it can be seen that the head 12 has been inserted into the rectum 24 through the sphincter 30. The head 12 is positioned by the rod 16 in proximity to the prostate 42. The prostate 42 is rubbed through the wall 44 of the rectum 40. The head 12 is designed so as to reside in close proximity to the prostate 42 when the head 12 is inserted through the sphincter 30. The rod 16 extends outwardly through the sphincter 30 and wraps around onto the perineum area 46. The rod 16 can be configured so as to apply pressure to the perineum area 46 at the same time that the head 12 is massaging the prostate 42. As such, the apparatus 10 massages the prostate 42 and also provides stimulation to the perineum area 46. Unlike U.S. Pat. Nos. 5,797,950 and 5,861,000 to the present inventor, the pressure applied to the perineum area 46 is reduced because of the counterpressures provided by the apparatus 10 relative to the sphincter 30.

The foregoing disclosure and description of the invention is illustrative and explanatory thereof. Various changes in the details of the illustrated construction may be made within the scope of the appended claims without departing from the true spirit of the invention. The present invention should only be limited by the following claims and their legal equivalents.

I claim:

1. An apparatus for massaging a prostate gland by a contraction of a sphincter comprising:

a body having a head and a resistor section means extending to an end of said body opposite said head, said head having a size suitable for fitting into a human rectum and through the sphincter, said head having a bulbous upper portion and a tapered section extending from said upper portion, said tapered section narrowing in diameter from said upper portion, said resistor section means connected to a bottom of said head, said resistor section means having a tapered surface widening from said bottom of said head, said tapered surface of said resistor section means having an angle of taper smaller than an angle of taper of said tapered section of said bottom of said head, said resistor section means having a widest diameter less than a widest diameter of said head, said resistor section means for movably retaining said tapered section within the sphincter.

2. The apparatus of claim 1, further comprising:

a rod connected to said end of said body.

* * * * *